(12) United States Patent
Wolfer et al.

(10) Patent No.: US 12,129,958 B2
(45) Date of Patent: Oct. 29, 2024

(54) HAND-HELD DEVICE FOR RECORDING OF LIVING SKIN AREAS OF HUMAN AUTOPODS AND DOCUMENTS

(71) Applicant: DERMALOG JENETRIC GMBH, Hamburg (DE)

(72) Inventors: Roberto Wolfer, Jena (DE); Holger Femel, Rothenstein (DE); Yvonne Vödisch, Jena (DE); Jörg Standau, Jena (DE)

(73) Assignee: DERMALOG JENETRIC GMBH, Jena (DE)

( * ) Notice: Subject to any disclaimer, the term of this patent is extended or adjusted under 35 U.S.C. 154(b) by 361 days.

(21) Appl. No.: 17/773,249

(22) PCT Filed: Oct. 29, 2020

(86) PCT No.: PCT/EP2020/080401
§ 371 (c)(1),
(2) Date: Apr. 29, 2022

(87) PCT Pub. No.: WO2021/084011
PCT Pub. Date: May 6, 2021

(65) Prior Publication Data
US 2022/0377164 A1 Nov. 24, 2022

(30) Foreign Application Priority Data
Oct. 30, 2019 (DE) .............. 20 2019 106 022.0

(51) Int. Cl.
*F16M 11/10* (2006.01)
*F16M 11/04* (2006.01)
(Continued)

(52) U.S. Cl.
CPC ........... *F16M 11/10* (2013.01); *F16M 11/041* (2013.01); *F16M 13/04* (2013.01);
(Continued)

(58) Field of Classification Search
CPC ...... F16M 11/10; F16M 11/041; F16M 13/04; F16M 2200/022; H04M 1/04; G06V 40/13; A61B 5/1172
See application file for complete search history.

(56) References Cited

U.S. PATENT DOCUMENTS 5,687,732 A * 11/1997 Inagaki .............. G04B 37/0016
600/490
6,699,188 B2 * 3/2004 Wessel ................... A61B 5/339
128/920

(Continued)

OTHER PUBLICATIONS

Internet citation "A Portable Scanner Alternative for the iPhone—ScanJig!," published on the world wide web on Dec. 8, 2016, available at the URL: https://ndassistive.org/blog/a-portable-scanner-alternative-for-the-iphone-scanjig/ last accessed Apr. 28, 2022.

(Continued)

*Primary Examiner* — Ernest G Tacsik
(74) *Attorney, Agent, or Firm* — Christensen, Fonder, Dardi & Herbert PLLC

(57) ABSTRACT

A hand-held device for recording of living skin areas of human autopods and documents is disclosed. The device has an image acquisition module with a support surface and a holding unit for a display and an operating module. The holding unit contains a base frame and a folding frame, which are pivotably connected by a mechanical pivot joint. The image acquisition module is arranged in the base frame, with the support surface facing the folding frame, and the display and operating module can be arranged in the folding frame, with the display facing away from the base frame. In an opened state of the holding unit, the base frame and the folding frame enclose an angle of less than 90° and greater than 20° with each other. In a closed state of the holding unit, the image acquisition module can be covered by the display and operating module.

15 Claims, 5 Drawing Sheets

(51) Int. Cl.
  *F16M 13/04*   (2006.01)
  *H04M 1/04*    (2006.01)
  *A61B 5/1172*  (2016.01)
  *G06V 40/13*   (2022.01)

(52) U.S. Cl.
  CPC ............ *H04M 1/04* (2013.01); *A61B 5/1172* (2013.01); *F16M 2200/022* (2013.01); *G06V 40/13* (2022.01)

(56)         References Cited

U.S. PATENT DOCUMENTS

```
 8,036,431   B1     10/2011  Fisher et al.
 8,150,485   B2 *    4/2012  Lee .................... H04M 1/0245
                                                         455/575.5
 8,211,364   B2 *    7/2012  Drucker ............ A61B 5/14532
                                                         422/50
2003/0089832 A1      5/2003  Gold
2015/0083615 A1      3/2015  Lay et al.
2017/0079592 A1 *    3/2017  Park ...................... G16H 40/60
```

OTHER PUBLICATIONS

International Search Report issued in PCT/EP2020/080401, to which this application claims priority, mailed Feb. 10, 2021, and English-language translation thereof.

* cited by examiner

HAND-HELD DEVICE FOR RECORDING OF LIVING SKIN AREAS OF HUMAN AUTOPODS AND DOCUMENTS

CROSS REFERENCE TO RELATED APPLICATIONS

This application is the U.S. 371 National Stage filing for PCT Application No. PCT/EP2020/080401, now published as WO 2021/084011, filed Oct. 29, 2020, which claims the priority to German Application No. DE 20 2019 106 022.0 filed on Oct. 30, 2019, the entirety of each of which is hereby incorporated by reference.

TECHNICAL FIELD

The disclosure relates to a hand-held device for recording living skin areas of human autopods and documents. It is used in particular for the identification of persons during mobile operations, at a routine control of suspicious persons, access or presence control at events or border control in trains, buses or airplanes. Due to its small size, compactness and the modular design, it can be permanently carried by control officers and is thus also spontaneously available for identification of persons at any location.

BACKGROUND

The mobile capture and identification of persons is steadily gaining in importance. For this purpose, identity documents (ID documents) and/or fingerprints of more than one phalanx is recorded with an image capture device and compared with databases. To record a person's fingerprints, the person places the fingers on a contact surface of the image capture device.

A concept for a mobile fingerprint reader is described in U.S. Pat. No. 8,036,431 B1, which is suitable to be brought by a control officer (e.g. border guard) to the persons to be identified. Regardless of the fact that this device is not designed to accommodate multiple fingers simultaneously, nor can documents be recorded over the same support surface, a control officer operating the device must always maintain the same position relative to the device during repeated use in order to comfortably view the display. In addition, a cover that at least protects the finger support surface is required for transport between uses.

SUMMARY

It is the object of the disclosure to find an improved hand-held device for receiving living skin areas of human autopods and documents.

This object is solved according to the disclosure by the features of the independent claims. Advantageous embodiments are indicated in the subclaims.

BRIEF DESCRIPTION OF THE DRAWINGS

The disclosure will be described in more detail below by means of an example of an embodiment.

The drawings show.

DESCRIPTION OF EXEMPLARY EMBODIMENTS

Figure 1A:
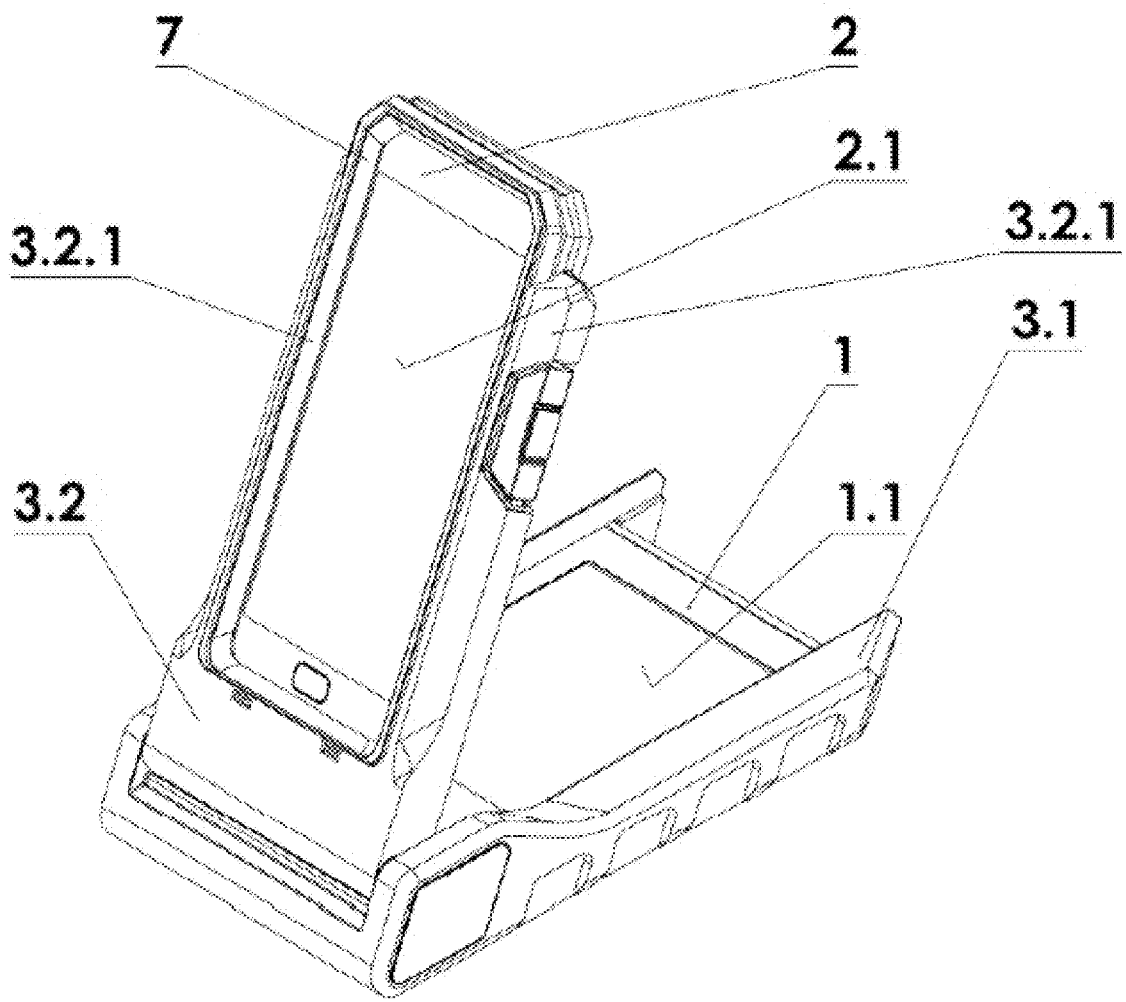
FIG. 1a a first exemplary embodiment of a device according to the disclosure in an unfolded or closed state, FIG. 1b the first exemplary embodiment of the device in a folded or closed state, FIG. 2 the individual modules of the first exemplary embodiment of the device, FIG. 3 an exploded view of the holding unit of the first exemplary embodiment of the device, and FIG. 4 the first exemplary embodiment of the device in the closed state with end piece.

All exemplary embodiments of a device according to the disclosure include, as shown in FIG. 1a, an image acquisition module 1 and a holding unit 3 for a display and operating module 2.

The image acquisition module 1 contains at least one optical, capacitive or ultrasound-based scanner and a support surface 1.1 on which the object to be scanned, in particular the fingers of a person, are placed to generate an image.

The image acquisition module 1 may further comprise a control unit, a memory unit, a data processing unit, and an internal power supply unit.

The display and operating module 2 contains at least one display 2.1, which can optionally be used as a touch screen for operating or controlling the image acquisition module 1. The display and operating module 2 can further comprise a control unit, a memory unit, a data processing unit and an internal power supply unit.

The optionally mentioned units may be present in the image module 1, the display and operating module 2, partly in both modules or externally, in neither of these modules. The image acquisition module 1 and the display and operating module 2 can be connected to each other via hardware signal or power lines and/or these can communicate with each other and possibly with third electronic modules only or partially via wireless connections.

The holding unit 3 comprises a base frame 3.1 and a folding frame 3.2, which can be folded towards each other by means of a mechanical pivot joint.

The mechanical pivot joint can be formed by a pivot axis 4 or two pins 4 (see FIG. 3), which are firmly connected to the folding frame 3.2 and mounted in the base frame 3.1, optionally in locking discs 8 inserted there.

The image acquisition module 1 is arranged in the base frame 3.1 in such a way that its support surface 1.1 faces the folding frame 3.2. The display and operating module 2 is arranged in the folding frame 3.2 so that its display 2.1 faces away from the base frame 3.1.

During operation, in which a control officer controls the image acquisition module 1 by inputs on the display and operating module 2 and views the display 2.1, the device is set up on a base or the control officer holds the device in one hand in an closed state (shown in FIG. 1a). To ensure that the device rests securely in the control operator's officer's, recesses can be formed on the base frame 3.1 into which he can grip with his fingers. In the closed state of the holding unit 3, the support surface 1.1 and the display 2.1 enclose an angle of less than 90° and greater than 20° with each other.

In addition or as an alternative to the recesses, an interface for a holding device, in particular for a camera handle, can be provided on a bottom of the base frame 3.1 to enable a user of the device to hold the device.

With this angle setting within the specified range, reasonable operation of the device is possible. The angles within this range allow comfortable viewing by the control officer and result in the person being able to keep their fingers in view, which is usually considered comfortable.

The specific angle that is set may depend on the height distance from the control officer's eye level at which the device is positioned or held by him during operation.

In the unfolded on opened state, the contact surface 1.1 is freely accessible for a person to place his or her fingers on. The person cannot easily look at the display 2.1 while his or her fingers are resting on the support surface 1.1 and therefore cannot view any control results or other information that may be displayed there.

Figure 1B:
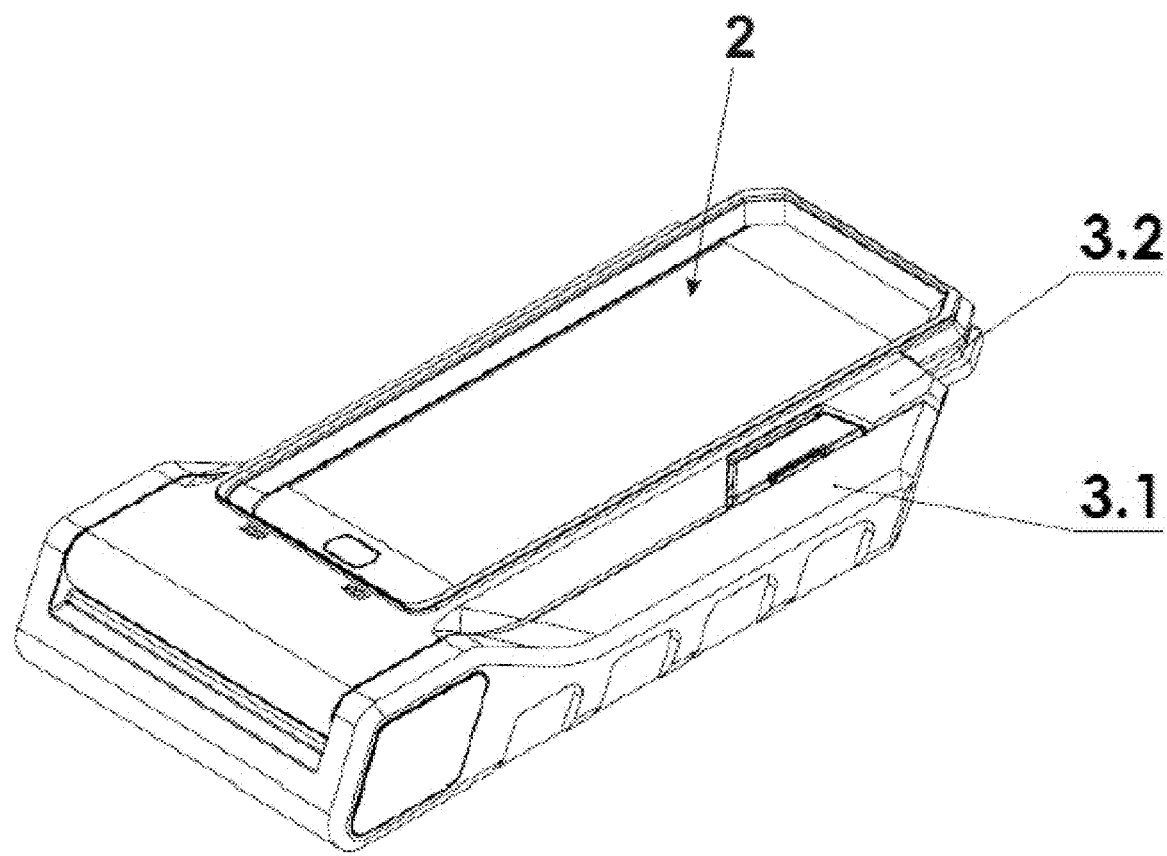

Outside of the operation of the device, the device can be in a folded or closed state of the holding unit 3, in which the image acquisition module 1 is covered by the display and operating module 2 and thus mechanically protected, see FIG. 1b. The closed state of the holding unit 3 is given when the folding frame 3.2 rests on the base frame 3.1 (not shown in the drawings) or, as can be seen in FIG. 1b, is located inside the base frame 3.1. The latter has the advantage that all mechanical forces acting laterally on the holding unit 3, which may act on it when handling the device outside of operation, are absorbed by the base frame 3.1, whereby no undesirable forces or moments can act on the pivot joint.

Figure 3:
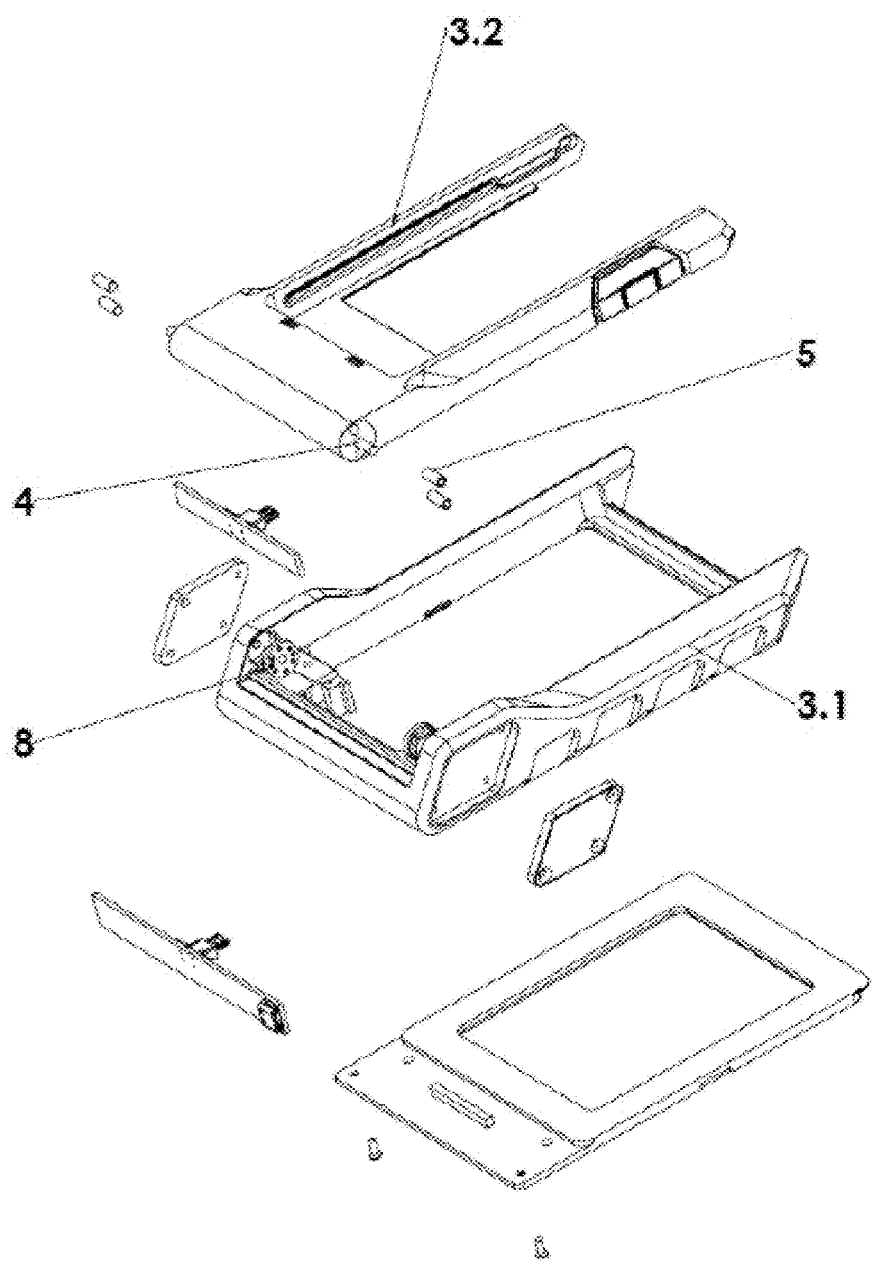

To ensure that at least one reproducible angle can be set between the display 2.1 and the support surface 1.1 for operation in routine positioning of the device with respect to the control officer, at least one latching element 5 is provided with a direction of action parallel to the axis of rotation 4, which is either mounted in the folding frame 3.2 and engaging in the base frame 3.1 or mounted in the base frame 3.1 and engaging in the folding frame 3.2. According to a first exemplary embodiment of the device, it has four locking elements 5, as shown in FIG. 3, which are each assigned in pairs to a locking disk 8 inserted in the base frame 3.1.

The locking discs 8 have an identical arrangement of recesses in which the locking elements 5 engage as soon as they come into a position aligned with this. The locking elements 5 can be resilient pressure pieces with a ball. During the angular adjustment between the folding frame 3.2 and the base frame 3.1, the ball slides on the plane surface of the locking discs 8 with tensioned spring until it comes into one of the recesses and engages in it with a partial relaxation of tensioned spring. The set angular position corresponds to a locked position. By pressing on the folding frame 3.2 in the direction of the base frame 3.1 or away from it, the control officer can set a further locking position or also close the holding unit 3. In this way, it is also possible to close the holding unit 3 without operating an additional control element.

The pressure required to change the locking position is selected to be at least high enough so that no change in the locking position occurs during normal operation of the display 2.1 by the control operator, in order to prevent an unintentional change in the locking position during use.

Figure 2:
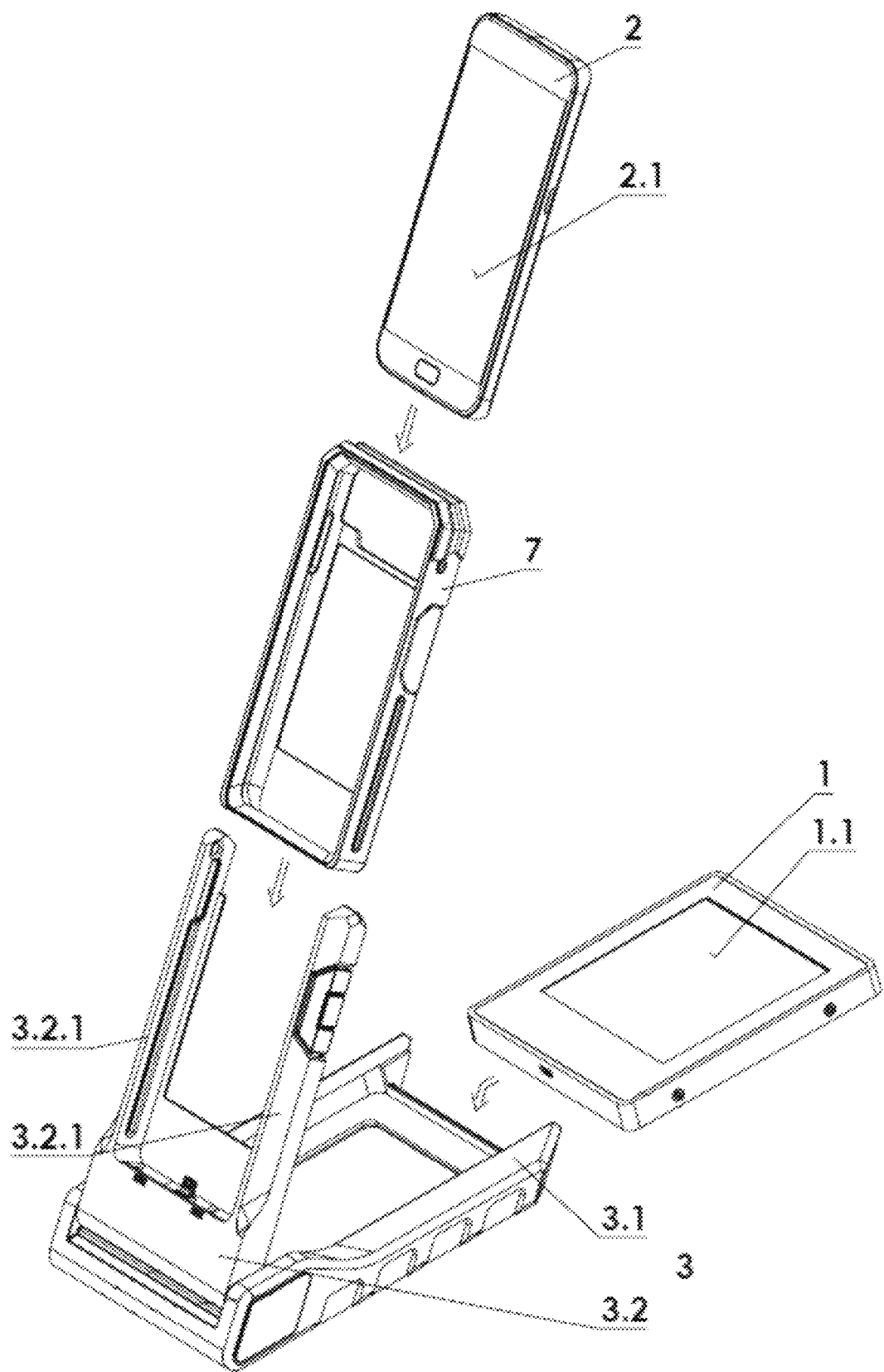

In order to insert the display and control module 2 into the holding unit 3 temporarily, e.g. only for the duration of a deployment of the control officer, the folding frame 3.2 can be designed in a U-shape with two parallel legs 3.2.1, between which the display and operating module 2 is arranged, as shown in FIG. 2. The display and operating module 2 can thus be easily pushed from the open side of the folding frame 3.2 into a reproducible position.

The display and operating module 2 can be a smartphone.

To make the holding unit 3 compatible for use with different smartphones, different adapter sleeves 7 can be provided for smartphones of different external dimensions, in each of which the smartphone is inserted, indirectly arranged in the folding frame 3.2.

The adapter sleeve 7 can be made of a flexible material, for example silicone or thermoplastic polyurethane (TPU), and can be frictionally connected to the folding frame 3.2 by being pressed between the two legs 3.2.1, enclosing the smartphone.

Commercially available smartphones have their operating elements, e.g. a volume control, a power button or a USB interface, at essentially the same locations on their circumferential surface, so that a respective assignment to corresponding operating elements on the holding unit 3 is possible via the adapter sleeve 7 or additional adapters.

Figure 4:
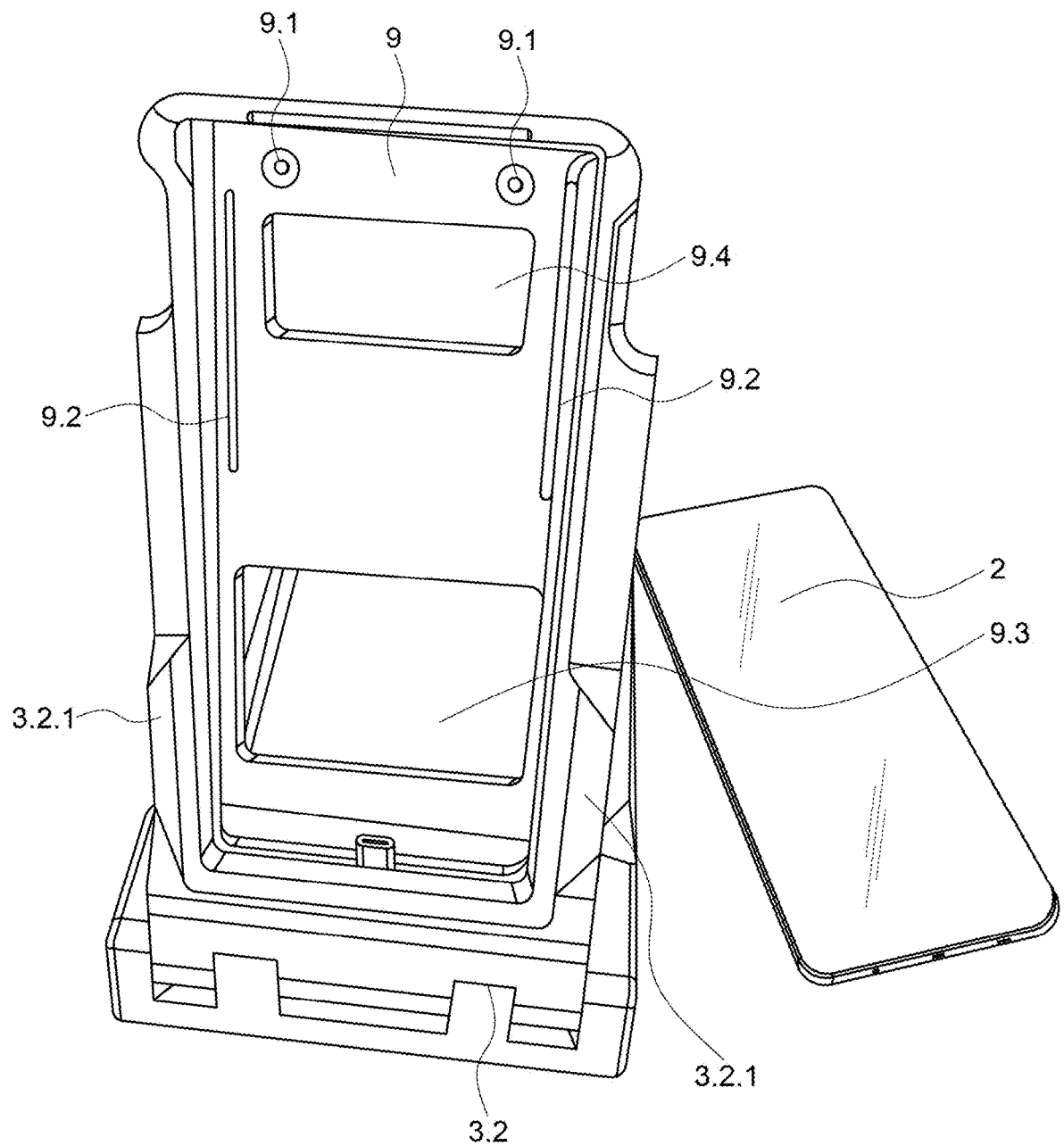

In addition or as an alternative to the adapter 7, the folding frame 3.2 can have an end piece 9 at its upper edge, which is connected to the folding frame 3.1, in particular removably, e.g. by means of one or more screw connections 9.1, as shown in FIG. 4.

The end piece 9 can be essentially L-shaped in cross-section so that it forms a housing for the display and control module 2 with the legs 3.2.1 of the folding frame 3.2 that is essentially O-shaped in cross-section.

The end piece 9 can be removed from the folding frame 3.2 to insert and remove the display and operating module 2.

It is also conceivable that the end piece 9 is additionally or alternatively designed to be flexible in such a way that it can be bent out of an insertion or removal direction of the display and operating module 2 for insertion and removal of the display and operating module 2 into or from the hinged frame 3.2. For this purpose, the end piece 9 may comprise an elastic material. Additionally or alternatively, a hinge can be provided to pivot the end piece 9 out of the insertion or removal direction of the display and operating module 2 for inserting and removing the display and operating module 2 into or from the hinged frame 3.2.

Additionally or alternatively, the end piece 9 may have two slots 9.2, each extending substantially parallel to the legs 3.2.1 of the folding frame 3.2, which may further assist the flexibility of the end piece 9.

It is also conceivable that the end piece 9 has a first or lower recess 9.3 that enables improved insertion and removal of the display and operating module 2 into or from the folding frame 3.2.

Also, the commercially available smartphones have an integrated camera with a lens that is essentially located in the same place near the top edge on the back of the smartphone.

In order to ensure the function of the camera even in a state integrated in the holding unit 3 of the smartphone, the integrated smartphone protrudes beyond the base frame 3.1 when the holding unit 3 is in the closed state, so that an area adjacent to an upper edge of the smartphone, in which the lens of an integrated camera is arranged, is not covered by the base frame 3.1. This enables the control officer to take an associated photo of a suspect or entrant before or after the fingerprint has been captured.

In the case of the provision of the end piece 9, a second or upper recess 9.4 can be provided in addition or as an alternative to the first or lower recess 9.3, so that the area adjacent to the upper edge of the smartphone in which the lens of the integrated camera is arranged is not covered by the end piece 9.

It is also conceivable that the image capture or acquisition module 1 is powered via a power supply present in the display and operating module 2. In the base frame 3.1 and/or in the image acquisition module 1, an electronic magnetic sensor can be arranged on a USB circuit board (not shown). In the folding frame 3.2, a pin magnet is arranged in a corresponding reference position to the magnetic sensor.

This causes the corresponding magnetic sensor on the base frame 3.1 and/or the image acquisition module 1 to automatically cut off the power supply of the image acquisition module 1 via an electronic switch formed by the magnetic sensor and the pin magnet when the folding frame 3.2 is folded shut when the image acquisition module 1 is not in use, thereby realizing a more energy-efficient device.

It is conceivable that the base frame 3.1, in particular on its outer sides where the recesses are formed, has an interface which makes it possible to supply the display and operating module 2 arranged in the folding frame with energy, in particular electrical energy. Additionally or alternatively, it is conceivable that data can be sent from the external computing device to the display and operating module 2 and/or received from it via an external computing device, in particular a computer, connected to the interface.

LIST OF REFERENCE SIGNS

1 Image acquisition module
1.1. Support surface
2 Display and operating module
2.1 Display
3 Holding unit
3.1 Basic frame
3.2 Folding frame
3.2.1 Leg
4 Rotary axis/pivot
5 Locking or latching element
7 Adapter sleeve
8 Locking disk
9 End piece
9.1 Screw connections
9.2 Slots
9.3 First or lower recess
9.4 Second or upper recess

The invention claimed is:

1. A hand-held recording system, the system comprising:
an image acquisition module having a contact surface for capturing living skin areas of human autopods and documents when in an opened state,
a display and operating module having a display, wherein the display and operating module controls the image acquisition module and receives images from the image acquisition module, and
a holding unit for the display and operating module,
wherein the holding unit includes a base frame and a folding frame which are connected to one another by a mechanical pivot joint and can be folded relative to one another via the pivot joint,
wherein the image acquisition module is arranged in the base frame with the support surface facing the folding frame,
wherein the display and operating module is arranged in the folding frame with the display facing away from the base frame, and
wherein, in the opened state of the holding unit, the base frame and the folding frame enclose an angle of less than 90° and greater than 20° with one another and, in a closed state of the holding unit, the image acquisition module is covered by the display and operating module.

2. The hand-held recording system according to claim 1, wherein the mechanical pivot joint is formed by a pivot axle and/or two pins which are firmly connected to the folding frame and are mounted in the base frame, in particular in locking discs inserted therein.

3. The hand-held recording system according to claim 2, wherein at least one locking element with a direction of action parallel to the pivot axis is present, which is either mounted in the folding frame and engaging in the base frame or is mounted in the base frame and engaging in the folding frame.

4. The hand-held recording system according to claim 3, wherein the at least one detent element is a resilient pressure piece with a ball.

5. The hand-held recording system according to claim 1, wherein in the closed state of the holding unit the folding frame lies at least partially within the base frame.

6. The hand-held recording system according to claim 1, wherein the folding frame is U-shaped with two mutually parallel legs, between which the display and operating module can be arranged.

7. The hand-held recording system according to claim 6, wherein the folding frame has at its upper edge an end piece which is connected to the folding frame and forms an O-shaped cross-section with the two mutually parallel legs of the folding frame.

8. The hand-held recording system according to claim 7, wherein the end piece:
is configured to be flexible so that it can be bent out of an insertion or removal direction of the display and operating module for inserting and removing the display and operating module into or from the folding frame,
has two slots each running essentially parallel to the legs of the folding frame,
has a first recess which is arranged at least partially in a lower half of the end piece, and/or
has a second recess which is arranged at least partially in an upper half of the end piece.

9. The hand-held recording system according to claim 1, wherein the display and operating module is a smartphone.

10. The hand-held recording system according to claim 9, wherein an adapter sleeve is provided in which the inserted smartphone can be arranged indirectly in the folding frame.

11. The hand-held recording system according to claim 10, wherein the adapter sleeve is made of a flexible material and is connected to the folding frame in a force-locking manner.

12. The hand-held recording system according to claim 9, wherein the smartphone can be arranged in such a way that it projects beyond the base frame in the closed state of the holding unit, so that an area adjacent to an upper edge on the back of the display and operating module, in which a lens of an integrated camera of the smartphone is arranged, is not covered by the base frame.

13. The hand-held recording system according to claim 1, wherein recesses are formed on the base frame which are arranged and designed in such a way that a person holding the holding unit can grip into the recesses of the base frame with their fingers, and/or an interface is provided on a bottom of the base frame, wherein the interface enables the person to hold the holding unit.

14. The hand-held recording system according to claim 13, wherein the holding unit is a camera handle.

15. The hand-held recording system according to claim 1, wherein an electronic magnetic sensor is present in the base frame and/or in the image acquisition module and a pin magnet associated with the magnetic sensor is present in the folding frame, whereby in the closed state of the holding unit the image acquisition module is disconnected from a power supply present in the display and operating module.

* * * * *